United States Patent [19]

Moulding, Jr.

[11] 4,005,707
[45] Feb. 1, 1977

[54] VARIABLE SIZE INTRAUTERINE CONTRACEPTIVE DEVICE

[76] Inventor: Thomas S. Moulding, Jr., 1954 Glencoe St., Denver, Colo. 80220

[22] Filed: May 30, 1975

[21] Appl. No.: 582,261

[52] U.S. Cl. .............................................. 128/130
[51] Int. Cl.² ........................................ A61F 5/24
[58] Field of Search ........... 128/130, 127, 260, 131

[56] References Cited
UNITED STATES PATENTS

| 3,659,596 | 5/1972 | Robinson | 128/130 |
|---|---|---|---|
| 3,734,090 | 5/1973 | Shubeck | 128/130 |
| 3,802,425 | 4/1974 | Moulding | 128/130 |
| 3,820,535 | 6/1974 | Marco | 128/130 |

*Primary Examiner*—Lawrence W. Trapp

[57] ABSTRACT

An intrauterine contraceptive device is provided which is inserted into a uterus in a collapsed position and held in expanded position by a locking means which prevents any further expansion of the IUD and limits the pressure exerted thereby on the uterine wall. The locking means, however, permits the IUD to collapse upon contraction of the uterus. The locking means may take the form of a string fixedly connected to one arm of the IUD and slidably attached to the other arm to be fixed in position upon initial expansion of the IUD by a quick setting adhesive or by means of an interengaging beaded chain and slot arrangement. The arms of the IUD can also be telescopically expandable in a longitudinal direction and fixed in expanded position once the ends of the arms come into engagement with the uterine wall but can collapse in response to uterine contractions.

14 Claims, 6 Drawing Figures

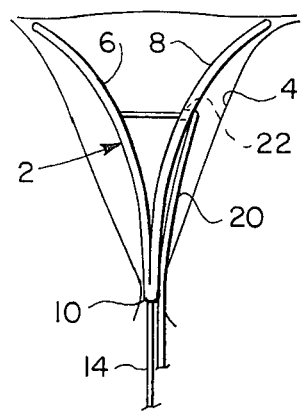
Fig._1
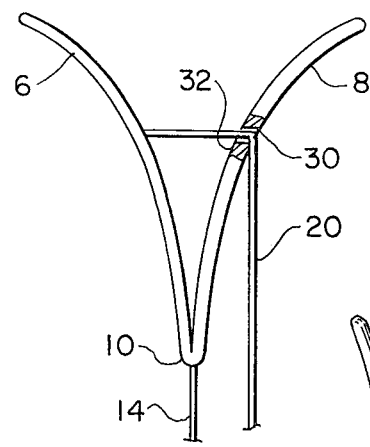
Fig._4
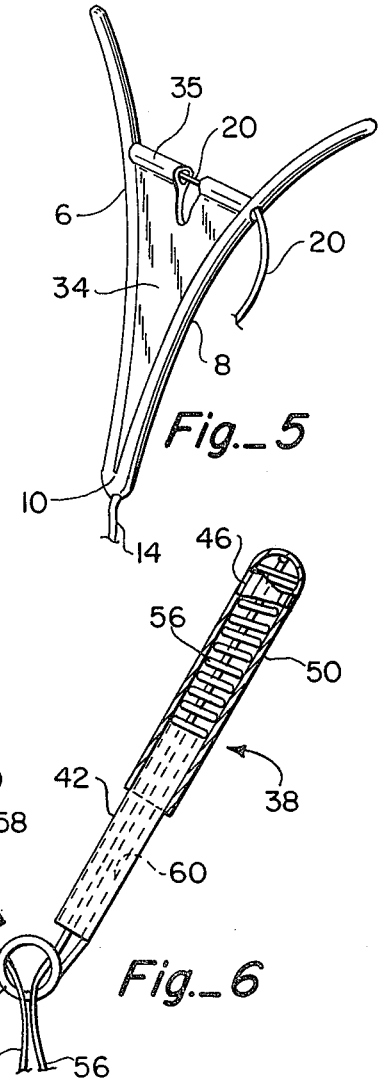
Fig._5
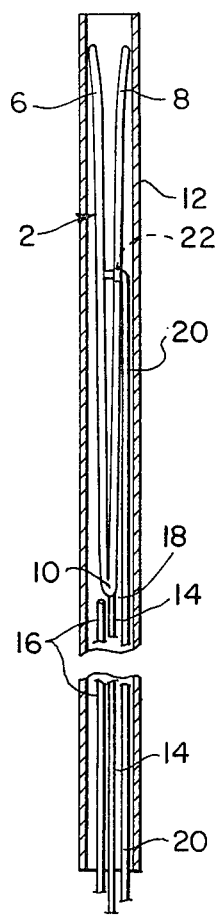
Fig._2
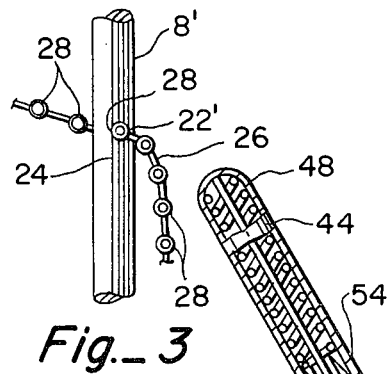
Fig._3
Fig._6

VARIABLE SIZE INTRAUTERINE CONTRACEPTIVE DEVICE

BACKGROUND OF THE INVENTION

1. Field of the Invention

This invention relates to an intrauterine contraceptive device, and more particularly to such a device which after initial expansion in the plane of the uterine cavity is locked to prevent further expansion but can contract upon contraction of the uterus.

2. Description of the Prior Art

As the effects of increased population become increasingly severe, resulting in environmental conditions which are deteriorating at an alarming rate, more and more effect is being placed on means for slowing the increase in world population, if not entirely halting such increase.

One type of contraception which has found considerable acceptance is the intrauterine contraceptive device, commonly known as an IUD. The IUD is a device which is placed inside the uterus, a soft tissue organ made primarily of smooth muscle. The way which it operates to prevent pregnancy is not entirely understood but it is well known that any foreign body placed in the uterus has a contraceptive effect which is 90 to 95 percent effective. However, some such devices which have been used have caused the wall of the uterus to become eroded or partially penetrated causing pain and bleeding to the user, thereby necessitating removal. In many instances the IUD's are expelled from the uterus and this is believed to be because they are not fitted properly, such as being too small, or otherwise not constructed to resist expulsion. However, when larger IUD's are used, there is a greater instance of pain and bleeding and sometimes the IUD induces unwanted contractions of the uterus.

IUD's have been constructed in numerous shapes and sizes and of various materials, but each has had certain deficiencies. One IUD was made by injecting silastic into the uterus which then set up to form a cast. However, this procedure was abandoned because of the high incidence of expulsions, probably due to the distention of the uterus in he anterior-posterior diameter. A popular form of IUD is the Lippes Loop which is a sinusoidal spring-like device which is stretched into a linear shape and inserted into the uterus after which it contracts to fill the uterine cavity, but lies only in one plane namely the plane of the uterine cavity and does not significantly expand the cavity in the anterior-posterior diameter. However, the constant resilient force against the walls of the uterus may cause abrading of the walls and eventual bleeding and even perforation.

One attempt to overcome these problem is shown in applicant's U.S. Pat. No. 3,802,425 which issued Apr. 9, 1974. This patent discloses a number of IUD's which can be introduced into the uterus in collapsed condition and expanded until the uterus is substantially filled whereupon they made rigid. Since these IUD's are rigid they will not cause constant pressure against the uterine wall and will resist expansion. However, Upon contraction of the uterus the user of the device might experience greater than usual discomfort and pain since the IUD will not collapse upon contraction of the uterus. Sustained contractions could result in abrasion of the uterine walls or embedding therein possibly creating medical problems.

An IUD is disclosed in U.S. Pat. No. 3,659,596 to Robinson in which the expansion of collapsible legs of an IUD are limited by a membrane extending therebetween. However, unless the IUD is perfectly sized to the uterus the desired result of having the IUD completely fill the uterus without either embedding into the uterine walls or being too small to completely fill the uterus will not occur. If the IUD is too large, the legs thereof will not expand until the membrane interconnecting them is drawn taut. Thus, the legs will continue to exert pressure on the uterine wall which can result in abrasion and embedding. On the other hand, if the IUD is too small even after the legs of the IUD are expanded they will not completely fill the uterus in the plane of the uterus because of the limitations of the outward movement thereof by the interconnecting membrane. This small size of the IUD increaases the chance of expuslsion.

SUMMARY OF THE INVENTION

In accordance with the present invention, a variable-sized IUD is provided which will substantially fill the uterus in the plane thereof and have a minimal thickness in the anterior-posterior direction. An angular member is provided having first and second legs interconnected at an acute angle and being bendable at the interconnection to a collapsed position to facilitate insertion of the device into the uterus and being expandable only in the plane of the uterus. Means is also provided in the member for expanding the member in the plane of the uterus until the legs engage the uterine wall irrespective of the size of the uterus in which the device is placed. Finally, means are provided to lock the legs to prevent further expansion thereof after they are in engagement with the uterine walls but permitting the legs to move toward the collapsed position upon contraction of the uterus.

More specifically, the IUD of this invention may comprise a Y or V-shaped IUD constructed of resilient material in which the legs of the V or Y are interconnected at an acute angle which is bendable for insertion of the device into the uterus, as with an insertion straw. In each embodiment the legs of the IUD are interconnected by a string which is fixedly attached at one end to one leg of the IUD and extends through an opening in the other leg of the IUD. A variety of means may be used after expansion of the legs in the IUD to fix them in the expanded position to limit the force exerted thereby on the intrauterine walls while still permitting the legs of the IUD to collapse together upon contraction of the uterus. Such locking means may take the form of a quick setting adhesive located in the aperture or adjacent thereto or even located on the portion of the string which will be in the aperture after expansion. The adhesive can also be provided in a capsule which can be ruptured by a sharp jerk on the string after expansion of the IUD. Alternatively, the string may include a series of spaced beads therealong and the aperture may be provided with an elongated slot at the lower end thereof so that after expansion the string can be pulled downwardly so that it is locked in the slot by adjacent beads.

If desired, a membrane can be provided between the legs of the IUD which is either sufficiently resilient so as to stretch when the IUD expands so that the expansion is not limited by the size of the membrane or alternatively the membrane may be made oversized so that it is sufficiently large to permit expansion of the IUD to fill any size uterus. The purpose of the membrane is to avoid any possibility of strangulation of the bowel should the IUD or its insertion cause perforation of the uterine wall whereby a portion of the bowel might extend through the triangular space between the legs and the spring.

An alternative embodiment is provided wherein the legs are not only spread apart but also are expandable longitudinally in the plane of the uterine cavity so that ends thereof firmly engage against the internal wall and after expansion in both directions are locked in place, as by a quick setting adhesive which fixes the strings to a portion of the legs of the IUD and prevents further longitudinal expansion of the legs. However, longitudinal contraction of the legs are still possible in response to uterine contractions.

Furthermore, the device can be utilized in such a way that the final expanded position of the IUD is slightly smaller than the size of the uterine cavity so as to further reduce the undesirable effects of embedding while not increasing or significantly the chance for expulsion.

Thus, it can be seen that by locking the arms of the IUD in expanded position with respect to any of the embodiments thereof, further expansion is prevented and pressure on the uterine wall is minimized to lessen the chance of eroding the uterine wall. Furthermore, should the uterus contract for any reason the IUD can collapse with the contraction and therefore minimize any pain or discomfort to the user.

Additional advantages of the invention will become apparent from the description which follows, taken in conjunction with the accompanying drawings.

BRIEF DESCRIPTION OF THE DRAWINGS

FIG. 1 is a front elevation of an IUD constructed in accordance with this invention and shown in expanded position in a uterus;

FIG. 2 is a longitudinal section through an insertion straw showing the IUD of FIG. 1 positioned therein together with a sound;

FIG. 3 is a fragmentary perspective view of one leg of an IUD showing an alternative locking construction which utilizes a beaded string and an aperture having a slot at one side thereof;

FIG. 4 is a front elevation, similar to FIG. 1, but showing an alternative locking means wherein adhesive is provided in a capsule located in the aperture;

FIG. 5 is a perspective view of a further alternative embodiment wherein a membrane is provided between the legs of the IUD; and FIG. 6 is a longitudinal section through a further alternative embodiment wherein the legs of the IUD are expandable in longitudinal as well as lateral direction.

DESCRIPTION OF THE PREFERRED EMBODIMENTS

In accordance with one form of this invention, an IUD is shown in FIG. 1 positioned in a uterus 4. Conveniently, the IUD is made of a material which is biomedically compatible with the uterus and includes a pair of legs 6 and 6 interconnected at a bend 10 which are resilient so that they tend to spread apart. To facilitate insertion of the IUD, it may be placed in an insertion straw 12 as shown in FIG. 2. Conveniently, a string 14 is attached to the bottom of the IUD at bend 10 which can be used to pull the IUD into straw 12 so that it assumes a collapsed position.

To insert the IUD the leading end of the insertion straw is introduced into the uterus and the IUD can be pushed out of the straw by means of a sound 16 having an aperture 18 at its leading end, as shown, for receiving string 14. The sound can be used to properly position the IUD with the end of legs 6 and 8 positioned against the fundus and the bend at the entrance to the uterus whereupon the insertion straw can be withdrawn and the sound later removed from the string 14. String 14 can then be clipped off probably with a short portion remaining outside the uterus for use in subsequent removal of the IUD. In the use of some embodiments the sound is not removed until certain procedures outlined later have been completed.

It will be apparent that the IUD is positioned in the uterus so it can expand in the lateral direction and that no expansion will occur in anterior-posterior direction. This expansion will occur until the legs 6 and 8 engage the walls of the uterus.

In accordance with this invention, a locking means is provided which includes a string 20 attached at one end to leg 6, as shown in FIG. 1, and extends through an aperture 22 in leg 8. Just prior to insertion a quick setting adhesive may be placed along the portion of string 20 which will be aperture 22 after expansion of the IUD in the uterus. The adhesive will remain solvent for sufficient length of time for the IUD to fully expand in the uterus but then will harden so that no further separation or expansion of legs 6 and 8 is possible. In this way, the amount of pressure on the uterine walls will be limited by the fixed length of string 20 between legs 6 and 8 and therefore will reduce the likelihood of embedding in the uterine wall. Furthermore, should the uterus contract, arms 6 and 8 will be permitted to collapse inwardly about bend 10 and thereby reduce any pain or discomfort to the user due to the intrauterine device during these contractions.

Alternatively, the lower portion of leg 8 could be hollow with an opening to the outside of the limb at the apex of the V and a second opening at its mid-portion in the same position as aperture 22. String 20 would pass through this hollow portion of the IUD. Just prior to insertion a quick setting adhesive could be added to the portion of the string 20 that extends below the IUD. This adhesive would set up inside of leg 8 after the IUD was in the uterus. By such a mechanism string 20 and leg 8 would be in contact with one another over a longer distance, thus increasing the chance that the adhesive bond will hold.

An alternative locking means is shown in FIG. 3 wherein a leg 8' of an IUD is provided with an aperture 22' having a downwardly extending slot 24. A string 26 has one end connected to the other arm of the IUD and extends through aperture 22'. Conveniently, the string is provided with a series of beads 28 so that after insertion and expansion of the IUD the string can be drawn into slot 24 by pulling downwardly on the end of the string so that it is locked in slot 24 between two adjacent beads 28. During the period of time when tension is being placed on string 26, the IUD is kept properly positioned in the uterus by a continuation of downward pressure on string 14 and holding sound 16 firmly within the uterus so that aperture 18 of sound 16 is at the apex of the IUD thus providing a means for keeping the IUD in proper position.

A still further locking means is shown in FIG. 4 wherein string 20 passes through a larger aperture 30 in leg 8 in which is positioned a capsule 32 which is filled with a self-hardening adhesive material. After the IUD has been inserted into the uterus and expanded, the string 20 can be pulled downwardly with a sharp jerk to rupture capsule 32 so that the adhesive flows out into aperture 30 and adheres the string to the aperture to limit further expansion of legs 6 and 8, as in the prior embodiments. Sound 16 and string 14 are used to keep the IUD properly positioned in the uterus while pulling on string 20 in the same manner described in the previous embodiment.

The act of pulling on string 20 can also be used to create a "locked" position of the device which is slightly smaller than the uterus, further reducing the problems associated with embedding in the uterine wall without a significant increase in the chance for expulsions. This can be accomplished as follows. After the IUD has been inserted into the uterus and has conformed to uterine anatomy, string 20 can be pulled back two or three millimeters and be held in that position while the quick setting adhesive material hardens. While doing this, the IUD would be held in the uterus with sound 16 and string 14 as described above. This method of making the IUD slightly smaller than the uterine cavity could be used for all embodiments of this invention except that described in FIG. 3.

A further embodiment is shown in FIG. 5 which is similar to FIG. 1 but a triangular membrane 34 which extends between legs 6 and 8 and string 20, is shown. The edge of the membrane not attached to the legs of the IUD is formed into tube 35 through which string 20 passes freely. The purpose of the membrane is to prevent possible strangulation of the bowel should the device perforate the uterus and enter the peritonial cavity. Advantageously, the membrane 34 can be constructed of material which is sufficiently resilient so as not to limit the outward movement of the legs 6 and 8. Thus, the outward movement of the legs will be limited only by the uterine wall. Alternatively membrane 34 can be constructed to be oversized for any uterus in which the device might be placed so as not to provide any limitation of the expansion of arms 6 and 8 about bend 10. In this case, it need not be made of resilient material.

In addition, string 20 could run between the tops of legs 6 and 8 with membrane 34 filling the entire space from the apex of the V to the top of the membrane formed by the string so as to provide a large surface area within the uterus which has been shown to be associated with low pregnacy rates.

The IUD of FIG. 6 expands both laterally and longitudinally and means is provided for limiting the longitudinal movement once the IUD has been expanded to fill the uterus. In this regard, the IUD of FIG. 6 includes legs 36 and 38 which are telescopic and comprise inner tubes 40 and 42 over which outer sleeves 44 and 46 are respectively received, as shown. Inner tube 40 and outer sleeves 44 are urged apart by coil spring 48 mounted in the outer sleeve and similarly inner tube 42 and outer sleeve, 46 are urged apart by coil spring 50.

The two legs 36 and 38 are interconnected by a spring 52 which forms the bend between the two legs and urges them apart. A first string 54 is attached to the inside upper end of outer sleeve 44 and extends downwardly through the coil spring 48 and inner tube 40 and past spring 52 as shown. Similarly, a second string 56 has one end attached to the inside upper end of outer sleeve 46 and extends through spring 50 and inner tube 42 and past spring 52 so that the two springs depend downwardly from the bend that joins legs 36 and 38.

This IUD may be placed in an insertion straw similar to straw 12 which collapses legs 36 and 38 toward each other and places spring 52 under tension. Strings 54 and 56 are then pulled downwardly to compress coil springs 48 and 50, respectively, and to shorten the length of legs 36 and 38. A sound similar to sound 16 with aperture 18 through which strings 54 and 56 are passed can be used to hold the IUD in the insertion straw while a downward force is exerted by pulling on the strings. After the device is inserted into the uterus and expelled from the straw by pushing on sound 16, spring 52 will cause the legs to expand laterally in the uterus while springs 48 and 50 will cause longitudinal expansion until the ends are positioned against the fundus. Conveniently, just prior to insertion a quick hardening adhesive can be placed on the portion of strings 54 and 56 which will be within passageways 58 and 60, respectively, after the legs have expanded. In this way, the length of the legs will be fixed so that they cannot expand further once they fill the uterus but should the uterus contract the legs can collapse longitudinally and of course they can collapse laterally toward each other due to the resilience of spring 52.

A locked position of the legs can be created in which they are slightly shorter than the position they occupy in the uterus, further reducing the problems of embedding in the uterine wall without a significant increase in the chance of expulsion. After the IUD has been inserted into the uterus and has conformed to the uterine anatomy, this can be accomplished by pulling on string 54 and 56 to contract legs 36 and 38 slightly while keeping the IUD in the proper position in the uterus. The IUD is held in that position until the quick setting adhesive has formed a permanent bond between strings 54 and 56 and passageways 58 and 60 of legs 36 and 38, thus creating a locked position of the legs in which they are slightly shorter than the uterus. In addition, the legs can shorten further in response to uterine contractions.

From the foregoing, the advantages of this invention are readily apparent. An IUD has been provided, which has locking means for limiting expansion of the device once it fills the uterus in the place of the uterine cavity but which will permit the IUD to collapse upon contraction of the uterus to reduce the possibility of pain and embedding in the uterine wall.

In one form of the invention a self-hardening adhesive on a string slidable through one leg of the IUD will fix its position after expansion. In another form, a beaded string and slot cooperate to fix the expanded position of the IUD. In a still further embodiment, a capsule of adhesive which can be ruptured after expansion, fixes the position of the IUD. Finally, an embodiment is disclosed having longitudinally extendable legs which can be fixed in expanded position by a self-hardening adhesive. In each instance, the IUD can collapse upon contraction of the uterus but is limited against further expansion. Also the IUD of each embodiment can be contracted slightly after insertion to reduce the problems of embedding in the uterine wall, as previously described, without greatly increasing the chance of expulsion.

The invention has been described in detail with particular reference to preferred embodiments thereof, but it will be understood that variations and modifications can be effected with the spirit and scope of the invention.

What is claimed is:

1. A variable-sized intrauterine contraceptive device for substantially filling the uterus in the plane thereof and having minimal thickness in the anterior-posterior direction, said device comprising:
   an angular member having first and second legs interconnected at an acute angle and being bendable at said interconnection to a collapsed position to facilitate insertion of said device into the uterus and being expandable in the plane of the uterus;
   means in said member for expanding said member in the plane of the uterus until said legs engage the uterine wall irrespective of the size of the uterus in which said device is placed; and
   means to lock said legs to prevent further expansion thereof after they are in engagement with the uterine walls but permitting said legs to move toward said collapsed position upon contraction of the uterus.

2. A variable-sized intrauterine contraceptive device, as claimed in claim 1, wherein said locking means includes:
   a string connected at one end to said first leg of said device and extending through an aperture in said second leg of said device; and
   securing means for locking said string in said aperture after expansion to prevent further expansion but permitting collapsing of said IUD upon contraction of the uterus.

3. A variable-sized intrauterine contraceptive device, as claimed in claim 2, wherein:
   said securing means includes a quick hardening adhesive to secure said string to said aperture.

4. A variable-sized intrauterine contraceptive device, as claimed in claim 2, wherein:
   one end of said string is attached to one of said legs, said string extending through an aperture in the other leg.

5. A variable-sized intrauterine contraceptive device, as claimed in claim 2, wherein:
   said securing mean includes:
   a notch extending from said aperture; and
   said string includes:
      spaced beads thereon which are engageable with said notch to limit further expansion of said IUD after it has expanded to fill the uterus.

6. A variable-sized intrauterine contraceptive device, as claimed in claim 2, wherein said locking means includes:
   a bead of adhesive in said aperture for fixedly attaching said string to said aperture after expansion.

7. A variable-sized intrauterine contraceptive device, as claimed in claim 2, further including:
   a membrane extending between said legs of said IUD and said string, said membrane being constructed so as not to limit the expansion of said legs.

8. A variable-sized intrauterine contraceptive device for substantially filling the uterus in the plane thereof and having minimal thickness in the anterior-posterior direction, said device comprising:
   an angular member having first and second legs interconnected at an acute angle and being bendable at said interconnection to a collapsed position to facilitate insertion of said device into the uterus and being expandable in the plane of the uterus, each of said legs comprising telescopic members which are expandable longitudinally after insertion in the uterus;
   means in each said leg for expanding said members longitudinally until said legs engage the uterine wall irrespective of the size of the uterus in which said device is placed; and
   means to lock said members to prevent further expansion of said legs after they are in engagement with the uterine walls but permitting said members to move toward said collapsed position upon contraction of the uterus.

9. A variable-sized intrauterine contraceptive device, as claimed in claim 8, wherein each of said telescopic members comprises:
   an outer sleeve telescopically receiving an inner tube;
   a spring within said outer sleeve having one end engaging of said outer sleeve and the other end engaging the end of said inner tube, said string being attached at one end to the end of said outer sleeve and extending through a passageway in said inner sleeve and past the acute angle joining the first and second legs; and
   a quick hardening adhesive on each of said strings positioned to be within said passageway ater expansion of said IUD in the uterus to adhere each of said strings to said respective passageways to hold said IUD in fixed, expanded position.

10. A variable-sized intrauterine contraceptive device for substantially filling the uterus in the plane thereof and having minimal thickness in the anterior-posterior direction, said device comprising:
    at least one leg comprising telescopic members which are expandable longitudinally after insertion in the uterus;
    means in said leg for expanding said members longitudinally until said leg engages the uterine wall irrespective of the size of the uterus in which said device is placed; and
    means to lock said members to prevent further expansion of said leg after it is in engagement with the uterine wall but permitting said members to move toward said collapsed position upon contraction of the uterus.

11. A variable-sized intrauterine contraceptive device for substantially filling the uterus in the plane thereof and having minimal thickness in the anterior-posterior direction, said device comprising:
    an angular member having first and second legs interconnected at an acute angle and being bendable at said interconnection to a collapsed position to facilitate insertion of said device into the uterus and being bendable in the plane of the uterus;
    means in said member for expanding said member in the plane of the uterus until said legs engage the uterine wall irrespective of the size of the uterus in which said device is placed;
    means to subsequently contract said legs slightly out of engagement with the uterine wall when the uterus is fully extended; and
    means to lock said legs to prevent further expansion thereof in said position out of engagement with the uterine wall but permitting said legs to move toward said collapsed position upon contraction of the uterus.

12. A variable-sized intrauterine contraceptive device for substantially filling the uterus in the plane thereof and having minimal thickness in the anterior-posterior direction, said device comprising:

at least one leg comprising telescopic members which are insertable in the uterus in a collapsed position and are expandable longitudinally after insertion in the uterus;

means in said leg for expanding said members longitudinally until said leg engages the uterine wall irrespective of the size of the uterus in which said device is placed;

means to subsequently contract said telescopic members slightly out of engagement with the uterine wall when the uterus is fully distended; and means to lock said members to prevent further expansion of said leg in said position slightly out of engagement with the uterine wall, but permitting said members to move toward said collapsed position upon contraction of the uterus.

13. A variable-sized intrauterine contraceptive device for substantially filling the uterus in the plane thereof and having minimal thickness in the anterior-posterior direction, said device comprising:

a member which is insertable in the uterus in a collapsed position and is expandable after insertion in the uterus;

means within said member for expanding said member until it engages the uterine wall irrespective of the size of the uterus in which said device is placed;

means to subsequently contract said member slightly out of engagement with the uterine wall when the uterus is fully distended; and means to lock said member to prevent further expansion in a position where it is slightly out of engagement with the uterine wall but permitting said member to move toward said collapsed position.

14. A variable-sized intrauterine contraceptive device for substantially filling the uterus in the plane thereof and having minimal thickness in the anterior-posterior direction, said device comprising:

a member which is insertable in the uterus in a collapsed position and is expandable after insertion in the uterus;

means within said member for expanding said member until it engages the uterine wall irrespective of the size of the uterus in which said device is placed; and means to lock said member to prevent further expansion in the position where it is in engagement with the uterine wall but permitting said member to move toward said collapsed position.

* * * * *